United States Patent
Gryzlov et al.

(10) Patent No.: US 12,428,621 B2
(45) Date of Patent: Sep. 30, 2025

(54) METHOD FOR OPTIMISING A PROCESS TO PRODUCE A BIOCHEMICAL PRODUCT

(71) Applicant: BULL SAS, Les Clayes-sous-bois (FR)

(72) Inventors: Dmitri Gryzlov, Reigate (GB); Jeroen Vermeulen, Madrid (ES); Ioannis Bistinas, Amsterdam (NL); Jurian Kuyvenhoven, Den Bosch (NL); Quentin Creed, Brighton (GB)

(73) Assignee: BULL SAS, Les Clayes-sous-Bois (FR)

( * ) Notice: Subject to any disclaimer, the term of this patent is extended or adjusted under 35 U.S.C. 154(b) by 713 days.

(21) Appl. No.: 17/851,212

(22) Filed: Jun. 28, 2022

(65) Prior Publication Data

US 2022/0411749 A1    Dec. 29, 2022

(30) Foreign Application Priority Data

Jun. 29, 2021 (EP) .................... 21182278

(51) Int. Cl.
*C12N 5/071* (2010.01)
*C12M 1/06* (2006.01)
(Continued)

(52) U.S. Cl.
CPC ........... *C12N 5/0602* (2013.01); *C12M 27/06* (2013.01); *C12M 41/12* (2013.01); *C12M 41/36* (2013.01);
(Continued)

(58) Field of Classification Search
CPC ..... C12N 5/0602; C12M 27/06; C12M 41/12; C12M 41/36; C12M 41/40; C12M 41/42;
(Continued)

(56) References Cited

U.S. PATENT DOCUMENTS

| | | |
|---|---|---|
| 2007/0059838 A1 | 3/2007 | Morrison et al. |
| 2020/0387818 A1 | 12/2020 | Chan et al. |
| 2022/0068440 A1* | 3/2022 | Mrziglod ............... G16C 20/70 |

FOREIGN PATENT DOCUMENTS

| | | | |
|---|---|---|---|
| CA | 3 112 860 | 3/2020 | |
| EP | 3 696 619 | 8/2020 | |
| WO | WO-2020058237 A2 * | 3/2020 | ........... G05B 13/048 |

OTHER PUBLICATIONS

European Search Report issued in EP21182278.8, dated Dec. 20, 2021 (7 pages).

* cited by examiner

*Primary Examiner* — Brian J. Sines
(74) *Attorney, Agent, or Firm* — ARCH IP Law, PC; Joseph J. Mayo (57) ABSTRACT

A method for optimizing a process (PROC) to produce a biochemical product (P) defined by a quality attribute, the process being controlled by an actuation parameter (C) and being monitored to get a measured value (T). The method includes training a predictive model (PRED) on a training database; and deploying the trained predictive model (PRED) to provide a correction actuation parameter (dC) when a predicted quality attribute (pQA) is out of a targeted quality attribute interval (QAmin, QAmax). The method also includes a step of designing a physical model of the process (PROC) able to provide a simulated quality attribute, the training database comprising simulated quality attributes computed from the physical model and experimental quality attributes computed from biochemical products (P) previously produced.

9 Claims, 3 Drawing Sheets

(51) Int. Cl.
  *C12M 1/34*  (2006.01)
  *C12M 1/36*  (2006.01)
  *G05B 13/02*  (2006.01)
  *G05B 13/04*  (2006.01)

(52) U.S. Cl.
  CPC ............ *C12M 41/40* (2013.01); *C12M 41/42* (2013.01); *C12M 41/48* (2013.01); *G05B 13/0265* (2013.01); *G05B 13/048* (2013.01)

(58) Field of Classification Search
  CPC .. C12M 41/48; G05B 13/0265; G05B 13/048; G05B 17/02; G06N 5/01; G06N 3/08
  See application file for complete search history.

METHOD FOR OPTIMISING A PROCESS TO PRODUCE A BIOCHEMICAL PRODUCT

This application claims priority to European Patent Application Number 21182278.8, filed 29 Jun. 2021, the specification of which is hereby incorporated herein by reference.

BACKGROUND OF THE INVENTION

Field of the Invention

Embodiments of the invention relate to optimization of a process to produce a biochemical product, in particular by suggesting corrections actions on the process to reach a targeted quality.

Description of the Related Art

New health challenges impose an increasing pace to develop and produce biochemical products as vaccines or adjuvants for vaccines. In one hand, it requires developing new processes, faster or more effective, and in another hand, it requires to produce the desired product at a targeted quality and/or quantity.

An artificial intelligence supervising a process can detect gaps between an expected processing state and a current processing state as well as suggesting mitigating actions to correct the current processing state. The artificial intelligence is trained over historical data obtained from previous running of the process or previously produced products. However, historical data of new processes or new products may be sparse and not sufficient to train the artificial intelligence in order to get accurate results.

BRIEF SUMMARY OF THE INVENTION

There is therefore a need to provide a solution able to suggest mitigating actions on a process with sparse data to be trained on.

According to at least one embodiment of the invention, this need is satisfied by providing a method for optimizing a process configured to produce a biochemical product, the quality of the biochemical product being defined by a quality attribute, the process being controlled by at least one actuation parameter and being monitored to get at least one measured value, the method comprising the following steps:
  training a predictive model of the process until it is able to provide a predicted quality attribute from a dataset comprising each actuation parameter and each measured value, the predictive model being trained on a training database comprising several training datasets, each training dataset comprising each actuation parameter and each measured value, and being associated with a corresponding quality attribute; and
  deploying the trained predictive model to provide a predicted quality attribute from a dataset comprising each actuation parameter and each measured value, and to provide at least one correction actuation parameter when the predicted quality attribute is out of a targeted quality attribute interval.

The method, according to one or more embodiments, is notable in that it comprises a step of designing a physical model of the process able to provide a simulated quality attribute from a dataset comprising each actuation parameter and each measured value, and in that the training database comprises simulated quality attributes computed from the physical model and experimental quality attributes computed from biochemical products previously produced by the process.

The method offers a way to train the predictive model on a database comprising enough data compared to a database comprising only historical data, according to one or more embodiments. Thanks to the physical model, the sparse training database can be filled with simulated data. This way, the training step provide an accurate predictive model. In the same time, in at least one embodiment, the physical model does not require reactants or goods and can decrease drastically the wastes. Moreover, solving the physical model to get simulated quality attributes can be performed in a short period of time and can therefore reduce the delay time before the realization of the training step.

The method according to at least one embodiment of the invention may also have one or more of the following characteristics, considered individually or according to any technically possible combinations thereof:
  the predictive model is trained in a supervised way, the predictive model being preferably a neural network, a classification/regression algorithm or a decision tree;
  a first subgroup of measured values comprises at least one value providing information on conditions under which the process runs, the first subgroup of measured values preferably comprising at least a temperature, a pressure or a fluid velocity;
  a second subgroup of measured values comprises at least one value assessing quantities used to compute the experimental quality attribute of the biochemical product;
  the method comprises, before the training of the predictive model, a selection of the predictive model among a set of predictive models, the selection comprising a training of each predictive model of the set on a subset of the training database and an analysis of each trained predictive model;
  the training step comprises the training of a plurality of instances of the predictive model on the training database and the comparison between each instance of the predictive model;
  the designing step comprises a setting of the physical model wherein at least one model is set, each model being an empirical model or a theoretical model;
  the designing step comprises a validation of the physical model wherein a correlation factor against experimental data of the process is determined for each model of the physical model, the correlation factor of each model of the physical model being determined independently from other models; and
  the designing step comprises a selection of the model of the physical model being used to perform the simulated quality attributes, the selection being based on correlation factor of each model of the physical model.

One or more embodiments of the invention relate to a computer program product comprising instructions which, when the program is executed on a computer, cause the computer to carry out the steps of the method according to at least one embodiment of the invention.

BRIEF DESCRIPTION OF THE DRAWINGS

Other characteristics and advantages of the invention will become clear from the description that is given thereof below, by way of indication and in no way limiting, with reference to the appended figures, among which.

For greater clarity, identical or similar elements are marked by identical reference signs in all of the figures. Reference sign "Xn-m", where n and m are integer indices, corresponds to all reference signs from Xn to Xm with increasing indices. For example, C1-3 corresponds to C1, C2 and C3.

DETAILED DESCRIPTION OF THE INVENTION

One or more embodiments of the invention relate to a method for optimizing a process configured to produce a biochemical product. The method allows to control more accurately the process to get a biochemical product matching a targeted quality.

Figure 1:
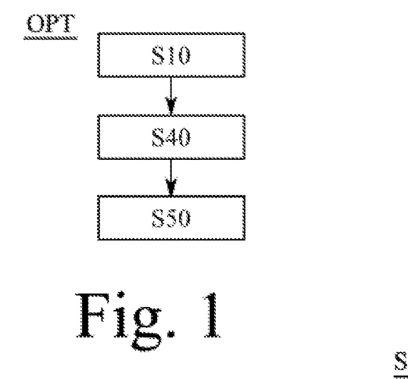
FIG. 1 is a flow diagram of a first example of a method for optimizing according to one or more embodiments of the invention.
Figure 4:
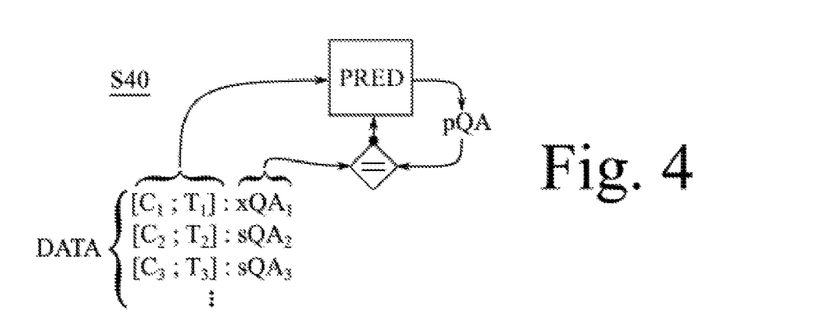
Figure 5:
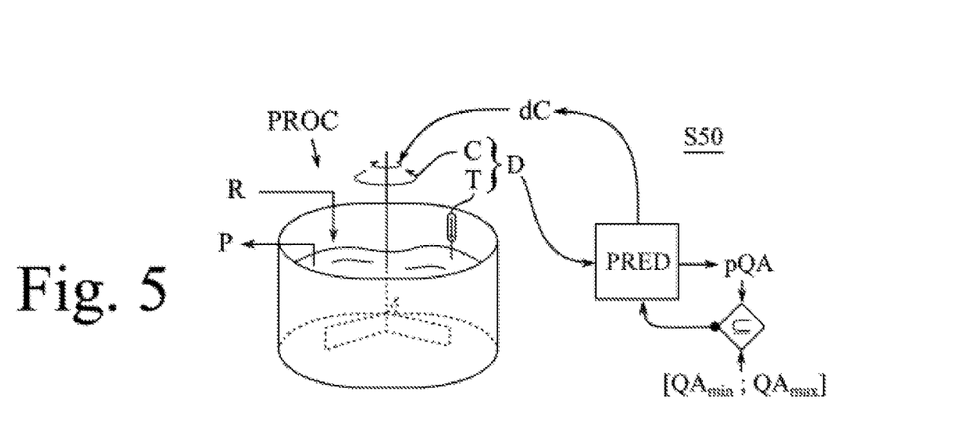

FIG. 1 shows the method OPT for optimizing the process, according to one or more embodiments of the invention. It comprises three main steps S10, S40, S50 performed sequentially. Each step S10, S40, S50 is illustrated by FIGS. 3, 4, 5.

Figure 2:
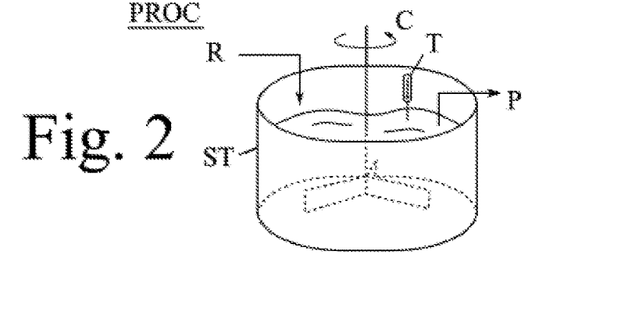
FIG. 2 is a first example of a process to optimize using the method for optimizing of FIG. 1, according to one or more embodiments of the invention.

FIG. 2 illustrates a simplified example of a process PROC to optimize, according to one or more embodiments of the invention. The process PROC is configured to produce a biochemical product P from, for example, a reactant R poured in a stirring tank ST. The process PROC is controlled by an actuation parameter C which is, in this case, the stirring speed of the stirring tank ST. The process PROC is also monitored to get a measured value T, for example the temperature in the stirring tank ST or the viscosity of the mixture. The quality of the biochemical product P is defined by a quality attribute which can be evaluated at the end of the process PROC. The quality attribute depends on operating conditions of the process PROC which comprise at least the actuation parameter C and the measured value T. To improve the knowledge on operating conditions, the measured value T is preferably monitored at different times and more preferably in a continuous way. To reach a targeted quality of the biochemical product P, one may try, during an initialization phase, different scenarii of stirring speed C and temperature T during the process PROC, selecting only the scenarii providing a biochemical product P reaching the targeted quality.

The method OPT, in at least one embodiment, allows to reduce the initialization time and the product waste by predicting the quality attribute of the biochemical product P before the process ends and by suggesting remediation actions if a mismatch between the predicted quality attribute and the targeted quality attribute is detected.

Figure 3:
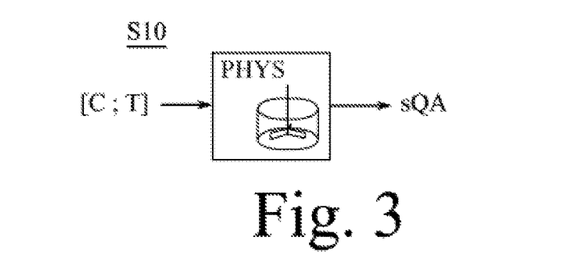
FIGS. 3, 4 and 5 are diagrams of a designing step, a training step, and a deploying step of the method for optimizing of FIG. 1, according to one or more embodiments of the invention.

To do so, by way of one or more embodiments, the method OPT comprises a step of designing S10 a physical model PHYS of the process PROC, the physical model PHYS being illustrated in FIG. 3. The physical model PHYS comprises different knowledge of the process as well as the effect of the actuation parameter C and the measured value T on it. For example, the physical model PHYS of the process PROC of FIG. 2 comprises theoretical knowledge on the reactions occurring in the stirring tank ST and the effect of the stirring speed C and the temperature T on the reaction speed. It can be reaction equations or abacus. It can also comprise a numerical model of the stirring tank ST to get a velocity field or a concentration of the species in the tank ST during the stirring. The physical model PHYS is designed to provide a simulated quality attribute sQA from a dataset, shown as [C; T] in FIG. 3, comprising the actuation parameter C and the measured value T.

The more accurate the physical model PHYS is, the better the optimizing will be. Therefore, in at least one embodiment, the physical model PHYS may be improved by comparing simulated quality attributes sQA with quality attributes of biochemical products obtained from previous runs of the process, under equivalent actuation parameters C and measured values T. A correlation factor can be computed from the comparison to track the improvements. The physical model PHYS may also be improved by comparing simulated quality attributes sQA with quality attributes of biochemical products previously obtained using other processes sharing some common features with the process to optimize as, for example, the same stirring tank ST.

When the physical model PHYS is set, by way of one or more embodiments, the method then comprises a step of training S40 a predictive model PRED of the process PROC, as illustrated in FIG. 4. The predictive model PRED is advantageously trained in a supervised way. For example, the predictive model PRED can be a neural network, a classification/regression algorithm or a decision tree.

The predictive model PRED is trained using a training database DATA comprising a plurality of training datasets of actuation parameters $C_{1-3}$ and measured values $T_{1-3}$. Each training dataset comprises each actuation parameters $C_{1-3}$ and each measured values $T_{1-3}$, shown in a form $[C_{1-3}, T_{1-3}]$ in FIG. 4, according to one or more embodiments of the invention. In the example of FIG. 2, according to one or more embodiments of the invention, the process PROC comprises one actuation parameter C and one measured value T. In this case, each training dataset comprises a set [C; T]. However, each training dataset of the training database DATA can comprise actuation parameters $C_{1-3}$ and measured values $T_{1-3}$ acquired at different times during a run of the process.

Each training dataset of actuation parameter $C_{1-3}$ and measured value $T_{1-3}$ is associated with a quality attribute xQA, sQA. The quality attribute is an experimental quality attribute xQA which is obtained from a previously obtained biochemical product or a simulated quality attribute sQA obtained from the physical model PHYS as described earlier. Each quality attribute $xQA$, $sQA$ is, of course, obtained under equivalent actuation parameters $C_{1-3}$ and measured values $T_{1-3}$ as the training dataset to which it is associated.

The predictive model PRED could be trained only on historical data, obtained from previous runs of the process. However, for new processes or products, the historical data may be too sparse to provide an accurate predictive model PRED. An amount of data high enough to train the predictive model PRED may require several runs of the process which imply wasting of goods and time. The main advantage of the method is to provide a way to train the predictive model PRED on enough datasets $[C_{1-3}; T_{1-3}]$ and quality attributes $sQA$, $xQA$ to provide an accurate predictive model PRED. The sparse database DATA is filled with simulated data thanks to the physical model PHYS. This way, the training step S40 can provide an accurate predictive model PRED. In the same time, the physical model does not require reactants or goods and can decrease drastically the wastes. Moreover, solving the physical model PHYS to get simulated quality attributes $sQA$ can be performed in a short period of time and can therefore reduce the delay time before the realization of the training step S40.

The training of the predictive model PRED is advantageously performed in a supervised way. A training dataset $[C_1; T_1]$ and the associated quality attribute $xQA_1$ is selected from the training database DATA and each actuation parameter $C_1$ and measured value $T_1$ is provided to the predictive model PRED. A predicted quality attribute $pQA$ is then provided by the predictive model PRED based on each actuation parameter $C_1$ and each measured value $T_1$. The predicted quality attribute $pQA$ is compared to the associated quality attribute $xQA_1$ and a feedback is provided to the predictive model PRED.

The predictive model PRED is trained until no additional improvements are made, for example when the predictive model PRED is accurate enough, or until a user stops the training. At this stage, the predictive model PRED is able to provide a predicted quality attribute $pQA$ from a dataset coming from the running process. The dataset coming from the running process comprises each actuation parameter and each measured value. The trained predictive model PRED is then deployed, as illustrated in FIG. 5 according to one or more embodiments of the invention, for example as an immutable executable, to provide predictions from datasets D coming from the process PROC. The process PROC runs preferably following an initial workflow. The initial workflow provides the value of the actuation parameter C at each instant of the process PROC. A user can, for example, follow the initial workflow and set different setpoints at different times on a device controlling the actuation of the process PROC, as the stirring speed. The control of the actuation parameter C is preferably carried out by a process controller, configured to follows the initial workflow. A dataset D comprising the actuation parameter C and the measured values T is provided to the predictive model PRED, for example by a user or preferably using acquisition interfaces. A predicted quality attribute $pQA$ is then generated by the predictive model PRED and then compared to a targeted quality attribute interval, for example corresponding to a lower quality attribute $QAmin$ and a higher quality attribute $QAmax$. If the predicted quality attribute $pQA$ belongs to the targeted interval then, the process PROC follows the initial workflow. However, if the predicted quality interval $pQA$ does not belong to the targeted interval, at least one correction parameter $dC$ is then provided by the predictive model PRED. Each correction parameter $dC$ is applied to a current actuation parameter C to correct the final quality attribute of the final product P. In the example of FIG. 5, according to one or more embodiments of the invention, the correction parameter $dC$ can be to increase/decrease the stirring speed C by a certain value or to start/stop the stirring. The correction parameters $dC$ can be applied by the user controlling the process or, preferably by the process controller. Instead of a correction parameter $dC$, the predictive model PRED can provide a setpoint to be reached by the actuation parameter C.

Figure 6:
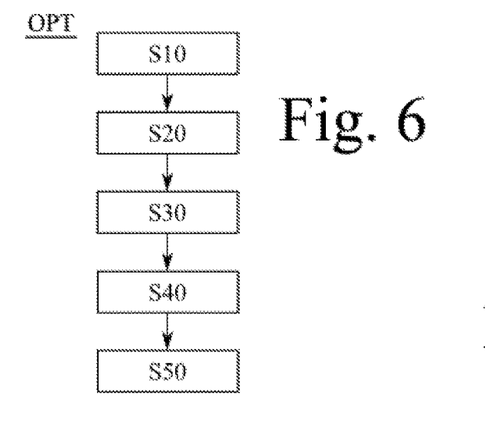
FIG. 6 is a flow diagram of a second example of the method for optimizing according to one or more embodiments of the invention.

The method OPT can comprise a creation of the training database S40, as illustrated in FIG. 6, according to one or more embodiments of the invention.

The creation S20 of the training database comprises an aggregation of data comprising datasets associated with experimental or simulated quality attributes. This data can be aggregated from various backend systems or resources. The aggregation can be performed automatically or by users as data engineers or data scientists. These data are collected, aggregated and, if necessary, transformed and cleansed. Experimental data comprise actuation parameters, measured values and associated experimental quality attributes from a previous run of the process. They may also come from different processes or products sharing common features (as a common microfluidic mixing chamber or a common stirring tank). Simulated data can comprise actuation parameters, measured values and the associated simulated quality attributes provided by the simulation of the physical model PHYS.

The creation S20 of the training database can also comprise the creation of a lightweight database. The lightweight database is a subset of the training database. The lightweight database is for example created from an exploration of the training database, also called full training database. During the exploration, users as data scientists or data engineers, can interact directly with the full training database to identify data called "features" that may be useful for future predictions and training. Features are datasets and the associated quality attributes the most representative of the process to optimize. The lightweight training database preferably comprise at least the features. The exploration can also comprise a cleaning of the lightweight training database. For example, simulated data covering experimental data may be removed to prioritized experimental ones. To simplify the work, the full training database and the lightweight database can be visualized. The visualizations can range from simple reports and dashboards to more advanced specialist mathematical charts and multidimensional graphs.

The method OPT can also comprise a selection S30 of the predictive model PRED, according to one or more embodiments of the invention. The predictive model PRED is selected among a set of predictive models including, for example, a neural network, a classification/regression algorithm or a decision tree. To select the predictive model PRED among the set, each predictive model of the set is trained and analyzed. The training is preferably performed on a subset of the full training database and preferably on the lightweight database. The analysis comprises preferably an assessment of the accuracy of each predictive model of the set. It can also comprise an assessment of the workload of the predictive models of the set. Each predictive model of the set can also be proofed against real-time data coming from a running process. However, during this proof, it is preferable that no correction is applied to the running process.

The selection S30 of the predictive model is performed before the training S40. However, during the training, an evaluation of the predictive model previously selected can be performed. A plurality of instances of the selected predictive model can be trained on the full training database and can then be compared with each other to evaluate a reproducibility or a robustness of the predictive model PRED. Metric performances, such as load balance, or model artifacts can also be monitored.

During the deploying step S50, the predictive model PRED may be deployed as service or as an immutable executable over a runtime environment. An approach is to create a microservice application that encapsulates the predictive model PRED and provides an access to it via a dedicated or a standard programming interface. The microservice application can then be packaged as an autonomous virtualization platform, for example a Docker™ container. This way, it ensures that the predictive model PRED can operate identically and consistently in any environment. The actuation parameter C and the measured value T can be collected from sensors installed on the equipment used by the process PROC. Sensors can be connected to the deployed predictive model PRED using stream services as an internet of things system.

Figure 7:
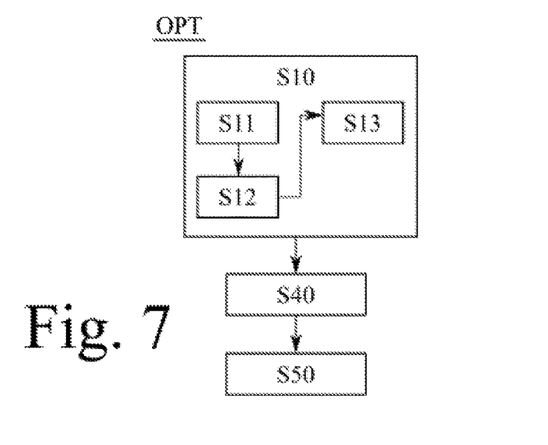
FIG. 7 is a flow diagram of a third example of the method for optimizing according to one or more embodiments of the invention.

FIG. 7 illustrates an implementation of the designing S10 of the physical model PHYS, according to one or more embodiments of the invention. The physical model PHYS comprises algorithms and/or equations used to capture the behavior of the process PROC and the system used by the process PROC. The simulation is the reproduction of the behavior of the process PROC and the system to get the outcomes of the physical model PHYS. The designing S10 comprises first a setting S11 of the physical model PHYS. The physical model PHYS can comprise an empirical model or a theoretical model.

An empirical model is built from a statistical analysis of observed data during previous runs of the process. The empirical model can be useful during the exploration of the full training database to detect deviant behaviors of the process PROC.

The physical model PHYS can also comprise a theoretical model, according to one or more embodiments of the invention. A theoretical model corresponds to a set of equations describing the behavior of the process PROC and, if relevant, the system used by the process PROC. The process PROC and the system can be modelled using partial differential equations or using lumped-element modelling. The theoretical model is preferably solved numerically using common methods adapted to said model. It can, for example, be a finite element method or a finite volume method. For example, the theoretical model can comprise a computational fluid dynamics model, commonly known as CFD model. It can also comprise a heat transfer model or a chemical model, both solved using a finite element method or a finite volume method.

The example of process of FIG. 2, according to one or more embodiments of the invention, takes place in a reactor and more specifically in a stirring tank ST. The theoretical model may comprise a CFD model to model the stirred fluid dynamics and a chemical model to model the reactions. The CFD model can provide velocity field of the stirred fluid, particles trajectories or space dependent concentrations of the reactants in the tank. The outcomes of the CFD model depend on parameters of the stirred fluid, as its viscosity or its density, on parameters of the stirring tank ST, as its size or the shape of the propeller and on operational conditions as the stirring speed or the fluid temperature. The chemical model can provide reaction speeds from space dependent concentrations of the reactants. The outcomes of the chemical model depend thus on CFD model outputs and temperature of the fluid. On more complex processes or systems, the theoretical model can also model pumps, heaters or filters.

Both, empirical and theoretical models are configured to provide a quality attribute of the biochemical product obtained using the process. However, the theoretical model may offer a better insight on the process PROC as it can be used to predict a quality attribute variation if the process PROC is modified or if it uses a different system. For example, the theoretical model can help to anticipate the effect of a reactor swap, from a stirring tank ST to a microfluidic mixer.

The theoretical model can also be configured to allow a real-time simulation. Real-time simulation means a simulation time short enough so the predictive model PRED can take into account variations of the actuation parameter and/or the measured value. For example, the theoretical model can be considered as configured to allow real-time simulation if it can be solved in less than 1 second. Real-time simulation may help to perform real-time prediction of a quality attribute of the biochemical product. It may also help to get visualization of the process PROC which can be convenient during the exploration of the training database.

The physical model PHYS can be validated S12 with a real test data to determine its accuracy. To do so, the empirical or theoretical model is validated S12 with experimental datasets generated by previous runs of the process. The validation S12 comprises a determination of a correlation factor between the experimental data and the model.

Figure 8:
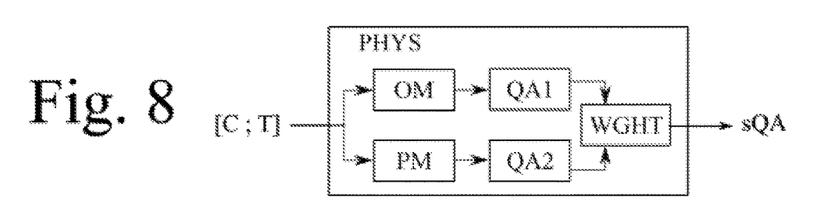
FIG. 8 is a diagram of the designing step of the method for optimizing of FIG. 7, according to one or more embodiments of the invention.

The physical model PHYS can comprise more than one model OM, PM, as shown in FIG. 8, according to one or more embodiments of the invention. It can comprise an empirical model OM and a theoretical model PM. Each model OM, PM is preferably set S11 and validated S12 independently from the others. Afterwards, knowing how each model OM, PM performs, the best model option is selected S13. The selection S13 only occurs if the physical model PHYS implements a plurality of models OM, PM. During the selection S13, only one of the models OM, PM can be selected. Therefore, the output of the physical model PHYS will depend on the selected model OM, PM. At least two models OM, PM can also be chosen as shown in FIG. 8, according to one or more embodiments of the invention. In this case, the outputs QA1, QA2 of each model OM, PM is preferably weighted WGHT to provide a more accurate simulated quality attribute sQA. The selection S13 is preferably performed on the basis of the correlation factor computed during the validation S12 of the physical model PHYS.

Figure 9:
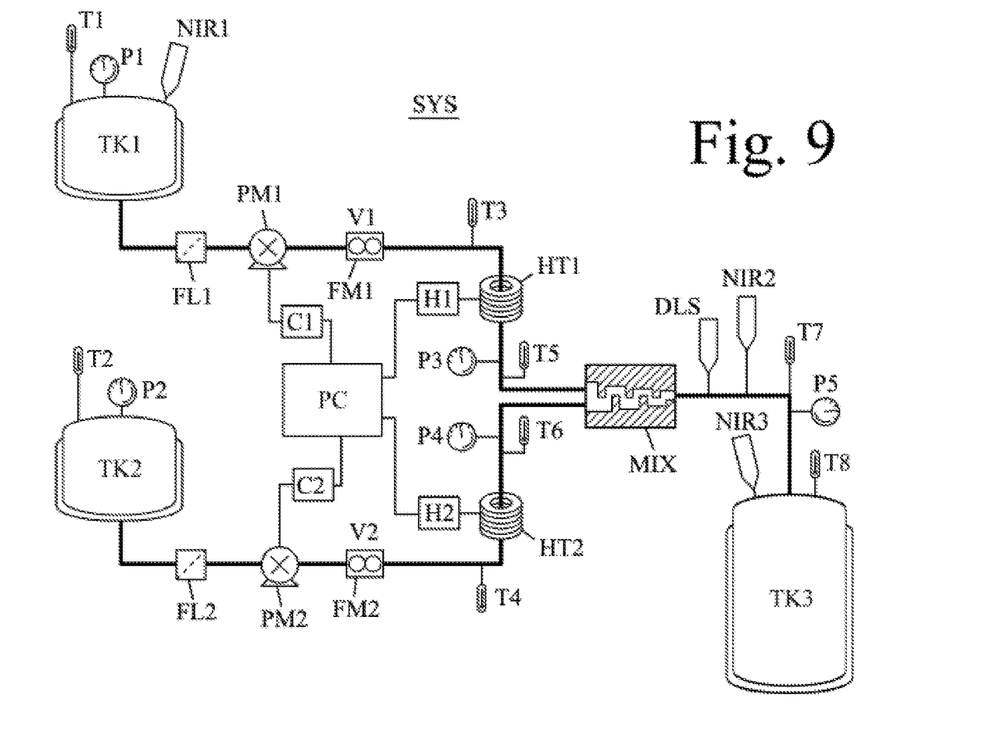
FIG. 9 is a second example of the process to optimize using the method for optimizing according to one or more embodiments of the invention.

The process PROC to optimize can use a production system SYS as illustrated in FIG. 9, according to one or more embodiments of the invention. In this example, the biochemical product is an adjuvant for a vaccine. The biochemical product comprises liposomes which are used to carry drugs or other substances into the tissues and can then be used as a vehicle for administration of nutrients and pharmaceutical drugs. Liposomes are small spherical sacs of phospholipid molecules enclosing a water droplet and having at least one lipid bilayer. Liposomes can be prepared by disrupting biological membranes (such as by sonication) or formed by a flash precipitation process in a microfluidic chamber (illustrated example). Liposomes most often comprises an aqueous phase material and an organic material such as phospholipids, especially dioleoyl phosphatidylcholine (DOPC), but it may also include other lipids, such as egg phosphatidylethanolamine and cholesterol. Produced liposomes may comprise different types defined by their sizes. The small liposomes are considered as a good candidate in an adjuvant for vaccines. The larger liposomes are, in contrary, considered as bad candidates. Therefore, a good quality adjuvant may comprise a large part of small liposomes rather than larger ones. The optimized process may than be able to produce a biochemical product comprising a large part of small liposomes.

The quality attribute of the biochemical product in this example can be defined by a distribution of sizes of the liposomes in the product. The more the distribution of sizes is centered on small sizes, the better is the biochemical product. The quality attribute can also comprise a concentration of liposomes or an indicator of the symmetry of the liposomes. The concentration of liposomes can also depend on sizes and symmetry of liposomes. It can also be a global concentration comprising all parameters of the liposomes. The quality attribute can comprise a plurality of indicators as the distribution of sizes or the concentration, preferably weighted such as to provide a global quality attribute of the biochemical product.

The production system SYS shown in FIG. 9, according to one or more embodiments of the invention, comprises a first, a second, and a third tank TK1, TK2, TK3. The first and second tanks TK1, TK2 are intended to contain the chemical reactants. The reactants may be an organic material, for example DOPC, and an aqueous phase material. The third tank TK3 is intended to contain the biochemical product delivered by the process, for example the adjuvant comprising SUV types of liposomes. A pipe runs from each of the first and second tanks TK1, TK2 to a mixer MIX. The mixing chamber MIX is intended to form the liposomes from the reactants. For example, it performs a flash precipitation process. In this example, the mixer MIX is a microfluidic chamber. Each pipe running form the first and second tanks TK1, TK2 comprises a filter FL1, FL2, a pump PM1, PM2, a flowmeter FM1, FM2, and a heater HT1, HT2. Those elements are intended to set the operating conditions of both reactants to produce the adjuvant at a targeted quality. The pumps PM1, PM2 and the heaters HT1, HT2 are controlled by a process controller PC. At each one of the pumps PM1, PM2 and the heaters HT1, TH2 correspond an actuation parameter C1, C2, H1, H2.

Temperatures T1-8 and pressures P1-5 of the reactants and the product are monitored at different positions of the production system SYS and at different steps of the process PROC. For example, temperatures T5, T6 of the reactants entering the mixing chamber MIX is measured to monitor operating conditions of the reaction taking place in the mixing chamber MIX. Velocities V1, V2 of the fluids are also monitored. Non-invasive measurements, as near infrared spectrometry measurements NIR1-3 and dynamic light scattering measurement DLS, are also performed at different points of the production system.

In the example of FIG. 9, according to one or more embodiments of the invention, the process PROC is monitored to get a plurality of measured values, comprising the temperatures T1-8, the pressures P1-5, the fluid velocities V1, V2, the near infrared spectrometry measurements NIR1-3 and the dynamic light scattering measurement DLS. The more measured values are monitored, the better is the insight of the process PROC.

A first subgroup of measured values, called operating conditions, provide information on the condition under which the process runs. It can comprise temperature, pressure and fluid velocities at the entrance or inside the mixing chamber MIX. Operating conditions has usually a strong influence on the reactions of the process and thus, on the product.

A second subgroup of measured values, called observation data, provide a better insight on the process as they can access data resulting from the physical or biochemical reaction as particle sizes or particle concentrations. Therefore they can be seen as a process signature. Observation data can comprise non-invasive measurements as near infrared spectrometry, dynamic light scattering, chromatography, gas analyzing or ultraviolet fluorescence. Observation data may comprise quantities used to compute the quantity attribute of the product, such as the particle sizes. This way, observation data can be meaningful for designing a physical model PHYS or training a predictive model PRED. As an example, according to one or more embodiments of the invention, observation data can comprise the distribution of liposome sizes at the output of the mixing chamber MIX.

The physical model PHYS of the process PROC using the production system can comprise a first theoretical model for the reactants and the product in the microfluidic mixing chamber MIX and a second theoretical model for the reactants and the product in the filters FL1, FL2, the pumps PM1, PM2, and/or the heaters HT1, HT2.

The first theoretical model of the microfluidic mixing chamber MIX can be called "cassette model" and can be set using drawings or three-dimensional plans of the mixing chamber MIX. The cassette model can take operating conditions as inputs, especially the temperature T5, T6, the pressures P3, P4 and fluid velocities V1, V2 of the reactants at the entrance of the chambre MIX. It can also take concentrations of species of the reactants as input. The cassette model can simulate the space-dependent concentrations of the reactants and the reaction speeds between said reactants. It allows to get distribution size or concentrations of particles such as liposomes and can thus allow to assess a quality attribute. The cassette model is preferably modelled using CFD and chemical modelling tools such as StarCCM+™ or MATLAB™. The cassette model can benefit a validation using production data comprising the operating conditions T1-8, P1-5, V1, V2, the observation data NIR1-3, DLS and the actuation parameters C1, C2, H1, H2. The validation can be performed by fitting simulation experimental curves of previous running of the process or values to model outputs.

The cassette model can be improved by using deep learning to adjust the parameters of said model. For example, according to one or more embodiments of the invention, a neural network can be configured to provide at least some parameters of the cassette model. The neural network can then be trained over previous results obtained using the production system, for example by using dummy fluids.

The second theoretical model can be set using datasheets of the different equipment FL1, FL2, PM1, PM2, HT1, HT2. The second theoretical model outputs comprise preferably the inputs of the cassette model, such as the temperature T5, T6, the pressures P3, P4 and fluid velocities V1, V2 of the reactants at the entrance of the chambre MIX. The inputs of the second theoretical model comprise preferably the actuation parameters C1, C2, H1, H2. The validation of the second theoretical model can be performed using production data such as operating conditions. The second theoretical model can be modelled using lumped element modelling, for example using Simcenter Amesim™.

Figure 10:
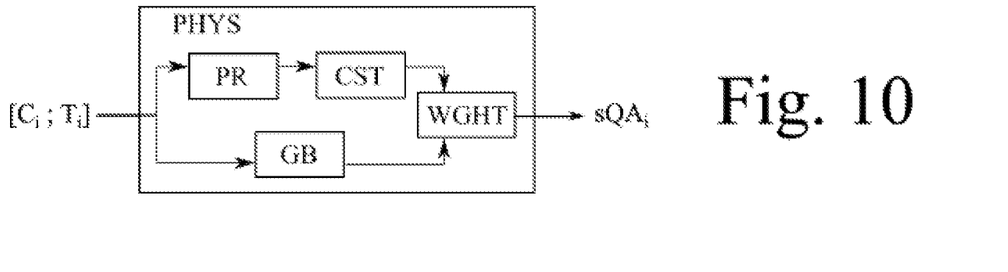
FIG. 10 is a diagram of the designing step of the method for optimizing of FIG. 7 applied to the second example of FIG. 9, according to one or more embodiments of the invention.

The physical model PHYS is illustrated in FIG. 10, according to one or more embodiments of the invention, and combines advantageously the cassette model CST and the second theoretical model PR to get a simulation of the full production system. The physical model PHYS can also combine an empirical model GB of the process and the production system, known as golden batch. The golden batch GB can be set using component analysis of the production system and validated by fitting curves over results obtained from previous runs. The golden batch GB is an empirical approach of the process and can provide an estimation of the quality attribute.

Depending on the use of the physical model PHYS, the theoretical models CST, PR or the golden batch GB can be preferred. For example, simulations can extrapolate results over range in which no experimental data are available. So during the selection and the evaluation of the predictive model, theoretical models CST, PR may be selected.

On the another hand, golden batch GB provide good agreement with experimental data. So, golden batch GB may be selected during the building and the exploration of the training database. It can, for example, help to detect incorrect data.

Figure 11:
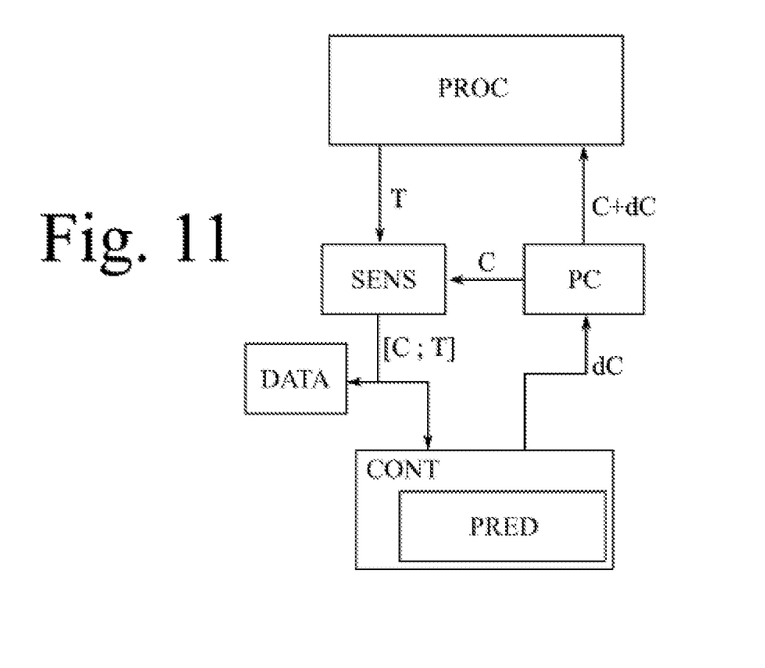
FIG. 11 is a third example of the process to optimize using the method for optimizing according to one or more embodiments of the invention.

FIG. 11 illustrates the interaction of the process PROC and the predictive model PRED to perform the optimizing of the process PROC, according to one or more embodiments of the invention. An acquisition interface SENS is in charge of acquiring each actuation parameter C and measure value T coming from the process PROC. The acquisition interface SENS can comprise a plurality of sensors distributed on the system used by the process PROC. The sensors can implement an internet of things network to send in an autonomous way each measured value T to the acquisition interface SENS. A process controller PC is in charge to control the running of the process PROC by providing each actuation parameter C to the process PROC. In case a correction dC is provided by the predictive model PRED, the process controller provides each corrected actuation parameter C+dC. The process controller PC can also send each actuation parameter C to the acquisition interface SENS.

The acquisition interface SENS sends a dataset [C; T] comprising each actuation parameter C and measure value T to the predictive model PRED. The acquisition interface SENS can also send the dataset [C; T] to a repository containing the training database DATA to improve said training database DATA for future training. The predictive model PRED runs on a specific runtime CONT such as a container.

The invention claimed is:

1. A method for optimizing a process configured to produce a biochemical product, a quality of the biochemical product being defined by a quality attribute, the process being controlled by at least one actuation parameter and being monitored to get at least one measured value, the method comprising:
designing a physical model of the process able to provide a simulated quality attribute from a dataset comprising each actuation parameter of said at least one actuation parameter and each measured value of said at least one measured value;
training a predictive model of the process until it is able to provide a predicted quality attribute from the dataset comprising said each actuation parameter of the at least one actuation parameter and said each measured value of the at least one measured value,
wherein the predictive model is trained on a training database comprising several training datasets, each training dataset of the several training datasets comprising said each actuation parameter and said each measured value, and being associated with a corresponding quality attribute,
wherein the training database further comprises simulated quality attributes computed from the physical model and experimental quality attributes computed from biochemical products previously produced by the process;
deploying the predictive model that is trained to
provide the predicted quality attribute from a dataset of the several training datasets comprising said each actuation parameter and said each measured value, and
provide at least one correction actuation parameter when the predicted quality attribute is out of a targeted quality attribute interval;
creating the training database comprising
an aggregation of data comprising the several training datasets,
a creation of a lightweight database comprising a subset of the training database, the lightweight database comprising datasets and quality attributes associated therewith, identified by users, representative of the process to optimize; and
selecting the predictive model among a set of predictive models, the selecting comprising a training of each predictive model of the set of predictive models on the lightweight database and an analysis of said each predictive model that is trained.

2. The method according to claim 1, wherein the predictive model is trained in a supervised way, and wherein the predictive model is a neural network, a classification/regression algorithm or a decision tree.

3. The method according to claim 1, wherein a first subgroup of measured values of said at least one measured value comprises at least one value providing information on conditions under which the process runs, the first subgroup of measured values comprising at least a temperature, a pressure or a fluid velocity.

4. The method according to claim 1, wherein a second subgroup of measured values of said at least one measured value comprises at least one value assessing quantities used to compute the experimental quality attributes of the biochemical product.

5. The method according to claim 1, wherein the training of the predictive model comprises training of a plurality of instances of the predictive model on the training database and a comparison between each instance of the predictive model.

6. The method according to claim 1, wherein the designing comprises a setting of the physical model wherein at least one model is set, each model of the at least one model being an empirical model or a theoretical model.

7. The method according to claim 6, wherein the designing further comprises a validation of the physical model, wherein a correlation factor against experimental data of the process is determined for each model of the physical model, and wherein the correlation factor of each model of the physical model is determined independently from other models.

8. The method according to claim 7, wherein the designing further comprises a selection of the each model of the physical model being used to perform the simulated quality attributes, wherein the selection is based on the correlation factor of said each model of the physical model.

9. A computer program product comprising instructions which, when the computer program product is executed on a computer, cause the computer to carry out a method for optimizing a process configured to produce a biochemical product, a quality of the biochemical product being defined by a quality attribute, the process being controlled by at least one actuation parameter and being monitored to get at least one measured value, the method comprising:

designing a physical model of the process able to provide a simulated quality attribute from a dataset comprising each actuation parameter of said at least one actuation parameter and each measured value of said at least one measured value;

training a predictive model of the process until it is able to provide a predicted quality attribute from the dataset comprising said each actuation parameter of the at least one actuation parameter and said each measured value of the at least one measured value, wherein the predictive model is trained on a training database comprising several training datasets, each training dataset of the several training datasets comprising said each actuation parameter and said each measured value, and being associated with a corresponding quality attribute, wherein the training database further comprises simulated quality attributes computed from the physical model and experimental quality attributes computed from biochemical products previously produced by the process;

deploying the predictive model that is trained to
provide the predicted quality attribute from a dataset of the several training datasets comprising said each actuation parameter and said each measured value, and provide at least one correction actuation parameter when the predicted quality attribute is out of a targeted quality attribute interval;

creating the training database comprising
an aggregation of data comprising the several training datasets, a creation of a lightweight database comprising a subset of the training database, the lightweight database comprising datasets and quality attributes associated therewith, identified by users, representative of the process to optimize; and selecting the predictive model among a set of predictive models, the selecting comprising a training of each predictive model of the set of predictive models on the lightweight database and an analysis of said each predictive model that is trained.

* * * * *